United States Patent [19]
Cook et al.

[11] 4,220,662
[45] Sep. 2, 1980

[54] GUANIDINOCYCLOHEXANECARBOXYLIC ACIDS

[76] Inventors: Elton S. Cook, 1842 Madison Rd., Cincinnati, Ohio 45206; Akira Fujii, 870-1 Sakaecho, Nishi-2, Matsudo, Japan

[21] Appl. No.: 927,058
[22] Filed: Jul. 24, 1978
[51] Int. Cl.$^2$ ............................................ A61K 31/195
[52] U.S. Cl. ................................................... 424/319
[58] Field of Search ......................................... 424/319

[56] References Cited
PUBLICATIONS

Chemical Abstracts 67: 30020g (1967).

Primary Examiner—Jerome D. Goldberg
Attorney, Agent, or Firm—Kinney & Schenk

[57] ABSTRACT

This invention pertains to antimecrobials effective in protecting against cocci and bacilli bacterial infections.

3 Claims, No Drawings

GUANIDINOCYCLOHEXANECARBOXYLIC ACIDS

BACKGROUND OF THE INVENTION

This invention pertains to antimicrobials effective in protecting against cocci and bacilli bacterial infections.

Although many antimicrobials have been suggested for the treatment of coccic and bacilli infections, such diseases continue to be a problem. The reason for this is that bacteria such as cocci and bacilli are a unique group of organisms embodying within themselves an array of yet unanswered puzzles in biology, both fundamental and experimental. They are ubiquitous in distribution and have attained extreme degrees of diversification in biological and biochemical characteristics. It is recognized that the significance of staphylococcal infections is not so much in severity, except in a few instances, as in the subtleties of the infection due to the unpredictable vagaries of these organisms.

Treatment of diseases caused by cocci and bacilli is complicated by the ability of the organisms to develop resistance. The magnitude of the problem is further amplified by the extreme difficulty of total eradication, and the frequent reappearance of the same strain even after apparently successful elimination. The inability to eliminate the carrier state by any of the currently known methods and the prevalence of the new antibiotic resistant hospital strains have added a new dimension to the frustrating situation. The development of such multiple antibiotic resistant strains of the organism suggests the desirability of investigating additional means of combatting the infections. As a consequence the development of antimicrobials which are effective against coccic and bacillic infections has attracted considerable attention.

As an example of the subtleties of coccic and bacillic infections, responses at different dose levels are confounding. Thus, in *Applied Microbiology*, Oct. 1968, p 1457, we show the effectiveness of 1-aminomethylcyclohexane-4-carboxylic acid. It would be presumed, therefore, that 1-aminocyclohexane-4-carboxylic acid would also be effective. Nevertheless at a 1 mg dose level we found 1-aminocyclohexane-4-carboxylic acid to possess relatively little antistaphylococcal activity. It can be seen that at low dose levels the antimicrobial activites of amino compounds relative to coccic and bacillic infections cannot be predicted.

SUMMARY OF THE INVENTION

As shown in the *Applied Microbiology* article the usual dose level for amino carboxylic acids is 5 mg. Consideration was given to guanidino derivatives of cyclohexane carboxylic acids as antimicrobials. However because of their poor solubilities in water, it was realized that only 1 mg doses of these substances could be readily administered. Quite surprisingly they were effective at this 1 mg dose level. In accordance with this invention therefore we have found that 4-guanidino- and 4-guanidinomethylcyclohexanecarboxylic acid are active in inducing resistance to such bacterial infections as cocci and bacilli. In addition at the 5 mg dose level 1-aminocyclohexane-4-carboxylic acid is a desirable anticocci agent.

DETAILED DESCRIPTION OF THE INVENTION

The processes of infection leading to coccic infections are accepted to be problems in the ecology of the parasite. It is being increasingly realized that the bacterial and host determinants are closely interrelated. Staphylococcal virulence derives from the combined action of several bacterial factors whose effectiveness is conditioned by the reactions of the host. Perhaps the most striking feature of host-parasite relationships in staphylococcal infections is the relatively atypical immumologic response. Human studies have given convincing evidence that most adult humans possess an array of anti-staphylococcal antibodies. Nevertheless resistance to staphylococcal infections seems to be governed to a considerable extent by other unrelated factors. For example, in the true sense the compounds employed herein are not antibiotics. In vitro tests show that these compounds do not kill the organism. However, quite surprisingly, in the system of the host they create an environment in which the organism does not grow. For this reason the compounds are called probiotics. The term probiotics has been proposed to designate compounds which build resistance to infection in the host, but do not inhibit the growth of microorganisms in vitro. Thus they unexpectedly render immunity to the host, as does a vaccine, but without the organism itself being present as it is in vaccines.

The compositions of this invention thus constitute a significant new class of antimicrobials. Specifically they are best represented by the formula

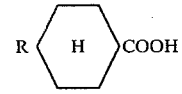

wherein the R substituent is $-NH_2$, $-NHC(NH)NH_2$, or $-CH_2NHC(NH)NH_2$. It is contemplated that they will be taken orally, or by intramuscular injection. These cyclohexanecarboxylic acids are not difficult to prepare. The 4-aminocyclohexane-1-carboxylic acid was prepared by hydrogenation under pressure in an autoclave of p-aminobenzoic acid in a mixture of water and platinum dioxide. The 4-guanidinocyclohexane-1-carboxylic acids were prepared by refluxing a mixture of the 4-amino- or 4-aminomethylcyclohexane-1-carboxylic acid, S-methylisothiourea hemisulfate, and concentrated ammonium hydroxide.

The resistance to staphylococcal infections obtained by these substituted cyclohexanecarboxylic acids will best be apparent from their biological effects in in vivo tests. In these in vivo tests antistaphylococcic activity was determined using BDF mice, both male and female. The animals were between 9 and 13 weeks old, males having approximate average weights of 12 to 19 grams, females having weights of 18 to 24 grams. For the most part the mice were raised and maintained on the Rockland diet.

The assays were conducted using a penicillin-resistant strain, *Staphylococcus aureus* Original, first isolated from a case of acute tonsilitis and maintained in our laboratories for years. This strain is preserved in the lyophilized form and stored at 0° C., and stock cultures were raised on SA 110 slants once in every 6 months. For testing, the inoculum was prepared as 24 hour cultures from Bactostaphylococcus Medium 110. The cells were washed and suspended in physiological saline (TC Tyrode Solution, Difco). In contrast to conventional procedures, a dose killing 80 to 90 percent ($LD_{80-90}$) instead of a dose killing 50 percent ($LD_{50}$) was used in these investigations. This has been the practice in our laboratories in studies with staphlococci since lower dosages often fail to give adequate degrees of mortality. The $LD_{80-90}$ was determined by injecting groups of mice subcutaneously with different dilutions of the bacterial suspension and noting the mortality over a 5-day period.

Using groups of six to ten mice, the animals were inoculated subcutaneously two hours before and four hours after challenge with a 60 percent suspension of the "Original Strain" organism. To provide a high dose of the guanidinocyclohexanecarboxylic acid derivatives which are not completely water soluble, a fine suspension is prepared in cottonseed oil (20mg/ml:dose, 0.25 ml). Antistaphylococcal activity in vivo is expressed as ASA and as effectiveness of protection using the $\chi^2$-test, and $ASA=[(M_c-M_e)/M_c]/C$, where $M_c$ is the mortality of untreated negative control, $M_e$ is the mortality of the experimental, and C is the dose per mol. Results of the tests are given in the following table.

| Antimicrobial | Protection (ASA) |
| --- | --- |
| 4-aminocyclohexanecarboxylic acid | 6.44 (5 mg dose) |
| 4-guanidinocyclohexanecarboxylic acid | 31.53 (1 mg dose) |
| 4-guanidinomethylcyclohexanecarboxylic acid | 33.70 (1 mg dose) |

It can be seen that the guanidino compounds were significantly effective in 1 mg doses. They were superior even to the 4-aminomethylcyclohexanecarboxylic acid referred to in the background of the invention (ASA 24.22).

The compositions of this invention thus constitute a significant new class of antistaphylococcal agents. It is contemplated that they will be taken orally, say in 250 to 500 milligram tablets. Where exposure to staphylococci or streptococci infections is likely, such as on entering a hospital, injections of say 150 to 500 mg will be prescribed. The cyclohexanecarboxylic acid antimicrobials can be combined with an aqueous vehicle, vegetable oil, monoglyceride or diglyceride for injection, sodium chloride being used if necessary to render the solution isotonic. The suspension or solution will contain 0.1 to 5 percent, preferably 0.1 to 1.5 percent of the antimicrobial by weight.

In the case of tablets, if desired, suitable colorants, adhesives, and lubricants will be incorporated along with a solid pharmaceutical diluent, for instance, starches, lactose, sucrose and other such diluents. These tablets will contain 50 to 75 percent of the amino or guanidinocyclohexanecarboxylic acid on a weight basis. Capsules can also be made. Thus, a process is provided for the control of infections in humans and other mammals due to cocci which involves administering to the mammal a pharmaceutically effective amount of the nitrogen-substituted cyclohexanecarboxylic acid compound. Various diluents, doses, and other variations and modifications will occur to those skilled in the art. Thus, it has been pointed out that tablets must be administered more frequently than injections. Such ramifications are deemed to be within the scope of this invention.

What is claimed is:

1. A method of treating bacterial infections in mammals comprising administering to a mammal suffering from said bacterial infection an antibacterially effective amount of the compound

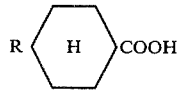

wherein the R substituent is selected from the group consisting of —NHC(NH)NH$_2$, and —CH$_2$NHC(NH)NH$_2$.

2. The method of claim 1 wherein the compound is 4-guanidinocyclohexanecarboxylic acid.

3. The method of claim 1 wherein the compound is 4-guanidinomethylcyclohexanecarboxylic acid.

* * * * *